(12) United States Patent
De Brouwer et al.

(10) Patent No.: US 11,026,634 B2
(45) Date of Patent: Jun. 8, 2021

(54) IMAGE-BASED SYSTEM AND METHOD FOR PREDICTING PHYSIOLOGICAL PARAMETERS

(71) Applicant: doc.ai incorporated, Palo Alto, CA (US)

(72) Inventors: Walter De Brouwer, Los Altos, CA (US); Apurv Mishra, San Francisco, CA (US); Samia De Brouwer, Los Altos, CA (US)

(*) Notice: Subject to any disclaimer, the term of this patent is extended or adjusted under 35 U.S.C. 154(b) by 262 days.

(21) Appl. No.: 15/946,629

(22) Filed: Apr. 5, 2018

(65) Prior Publication Data

US 2018/0289334 A1    Oct. 11, 2018

Related U.S. Application Data

(60) Provisional application No. 62/481,691, filed on Apr. 5, 2017.

(51) Int. Cl.
*G06K 9/62* (2006.01)
*A61B 5/00* (2006.01)
(Continued)

(52) U.S. Cl.
CPC .......... *A61B 5/7275* (2013.01); *A61B 5/0077* (2013.01); *A61B 5/1032* (2013.01); *A61B 5/1072* (2013.01); *A61B 5/441* (2013.01); *A61B 5/4872* (2013.01); *A61B 5/7267* (2013.01); *G06K 9/00275* (2013.01); (Continued)

(58) Field of Classification Search
CPC ... A61B 5/7275; A61B 5/0077; A61B 5/1032; A61B 5/4872; A61B 5/7267; A61B 5/441; A61B 5/1072; A61B 5/02405; G16H 50/30; G16H 30/40; G06K 9/4628; G06K 9/6271; G06K 9/00275; G06N 7/005;
(Continued)

(56) References Cited

U.S. PATENT DOCUMENTS 8,543,428 B1* 9/2013 Jones, III .............. G06Q 40/08
                                                     705/4
9,839,376 B1* 12/2017 Ross .................... A61B 5/6898
(Continued)

OTHER PUBLICATIONS

Yusuf Aytaret al.,"Face-to-BMI: Using Computer Vision to Infer Body Mass Index on Social Media", Proceedings of the Eleventh International AAAI Conference on Web and Social Media, pp. 572-575 (ICWSM 2017).*
(Continued)

*Primary Examiner* — Samir A Ahmed
(74) *Attorney, Agent, or Firm* — Haynes Beffel & Wolfeld; Ernest J. Beffel, Jr.

(57) ABSTRACT

System and method for determining physiological parameters of a person are disclosed. A physiological parameter may be obtained by analyzing a facial image of a person, and determining, from the facial image, a physiological parameter of the person by processing the facial image with a data processor. A neural network model such as regression deep learning convolutional neural network is used to predict the physiological parameter. An image processor screens out images which can't be recognized as facial images and adjust facial images to frontal facial images for predicting of physiological parameters.

26 Claims, 10 Drawing Sheets

(51) Int. Cl.

| | | |
|---|---|---|
| *G06K 9/00* | (2006.01) | |
| *A61B 5/107* | (2006.01) | |
| *G06N 5/04* | (2006.01) | |
| *G06N 3/08* | (2006.01) | |
| *A61B 5/103* | (2006.01) | |
| *G16H 50/30* | (2018.01) | |
| *G06K 9/46* | (2006.01) | |
| *G06N 3/04* | (2006.01) | |
| *G16H 30/40* | (2018.01) | |
| *A61B 5/16* | (2006.01) | |
| *A61B 5/024* | (2006.01) | |
| *G06N 7/00* | (2006.01) | |
| *G06N 20/10* | (2019.01) | |

(52) U.S. Cl.
CPC ....... *G06K 9/00288* (2013.01); *G06K 9/4628* (2013.01); *G06K 9/6271* (2013.01); *G06N 3/0454* (2013.01); *G06N 3/082* (2013.01); *G06N 5/046* (2013.01); *G16H 30/40* (2018.01); *G16H 50/30* (2018.01); *A61B 5/024* (2013.01); *A61B 5/02405* (2013.01); *A61B 5/163* (2017.08); *A61B 5/442* (2013.01); *G06K 2009/00322* (2013.01); *G06N 7/005* (2013.01); *G06N 20/10* (2019.01)

(58) Field of Classification Search
CPC ...... G06N 20/10; G06N 3/0454; G06N 5/046; G06N 3/082
See application file for complete search history.

(56) References Cited

U.S. PATENT DOCUMENTS

| | | | |
|---|---|---|---|
| 2015/0213207 A1* | 7/2015 | Amarasingham | G16H 40/20 705/2 |
| 2015/0339523 A1* | 11/2015 | Tsunematsu | G06T 7/70 382/103 |
| 2016/0253549 A1* | 9/2016 | Ramic | G06K 9/00281 382/118 |
| 2017/0206691 A1* | 7/2017 | Harrises | G02B 27/0172 |
| 2019/0082211 A1* | 3/2019 | Vats | G06F 3/011 |

OTHER PUBLICATIONS

Lingyun Wen et al. "A computational approach to body mass index prediction from face images" Image and Vision Computing 31 (2013) pp. 392-400.*

* cited by examiner

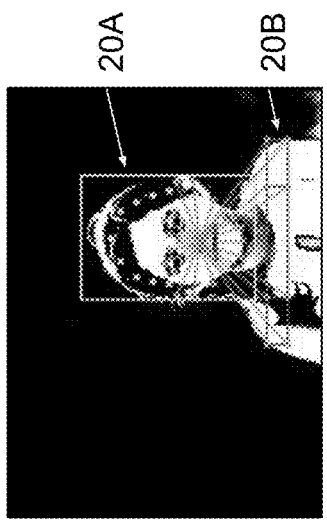
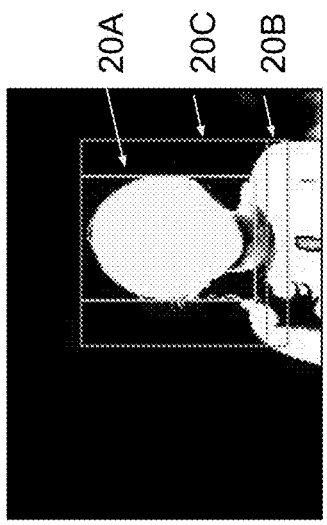
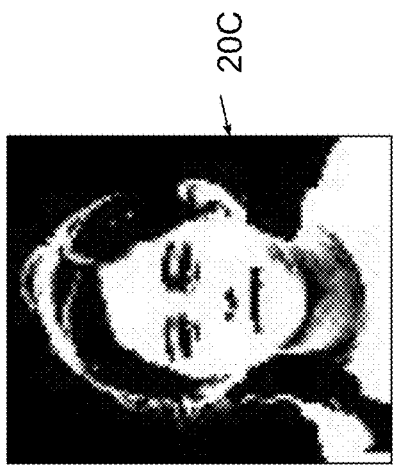
FIG. 2B

| name | Layer | Input x Output dimensions | Activation | Parameter/Spatial dimensions |
|---|---|---|---|---|
| conv1 | SpatialConvolution | 3x96 | ReLU | 11x11x4x4 |
| cccp1 | SpatialConvolution | 96x96 | ReLU | 1x1x1x1 |
| cccp2 | SpatialConvolution | 96x96 | ReLU | 1x1x1x1 |
| pool1 | SpatialMaxPooling | 3x3 | n/a | 2x2 |
| conv2 | SpatialConvolution | 96x256 | ReLU | 1x1x1x1 |
| cccp3 | SpatialConvolution | 256x256 | ReLU | 1x1x1x1 |
| cccp4 | SpatialConvolution | 256x256 | ReLU | 1x1x1x1 |
| pool2 | SpatialMaxPooling | 3x3 | n/a | 2x2 |
| conv3 | SpatialConvolution | 256x384 | ReLU | 1x1x1x1 |
| cccp5 | SpatialConvolution | 384x384 | ReLU | 1x1x1x1 |
| cccp6 | SpatialConvolution | 384x384 | ReLU | 1x1x1x1 |
| pool3 | SpatialMaxPooling | 3x3 | - | 2x2 |
| drop | Dropout | - | - | 0.75 |
| conv4 | SpatialConvolution | 384x512 | ReLU | 1x1x1x1 |
| cccp7 | SpatialConvolution | 512x1024 | ReLU | 1x1x1x1 |
| cccp8 | SpatialConvolution | 1024x2 | ReLU | 1x1x1x1 |
| pool4 | SpatialAveragePooling | 6x6 | - | 1x1 |

FIG. 7A

| Parameter | Value | Detail |
|---|---|---|
| Epochs | 10 | Number of times the entire dataset is forwarded through the network. |
| Batch Size | 512 | Number of images forwarded through network to make a single iteration for SGD. See Batch Learning (A. Rostamizadeh, A. Agarwal, and P. Bartlett 2011) for more details |
| Optimization | SGD | Stochastic Gradient Descent (SGD) |
| Learning | -- | Backwards Propagation (BackProp) |
| Learning Rate | 0.03 | For SGD |
| Momentum | 0.9 | For SGD |
| Weight Decay | 0.0004 | For SGD |

FIG. 7B

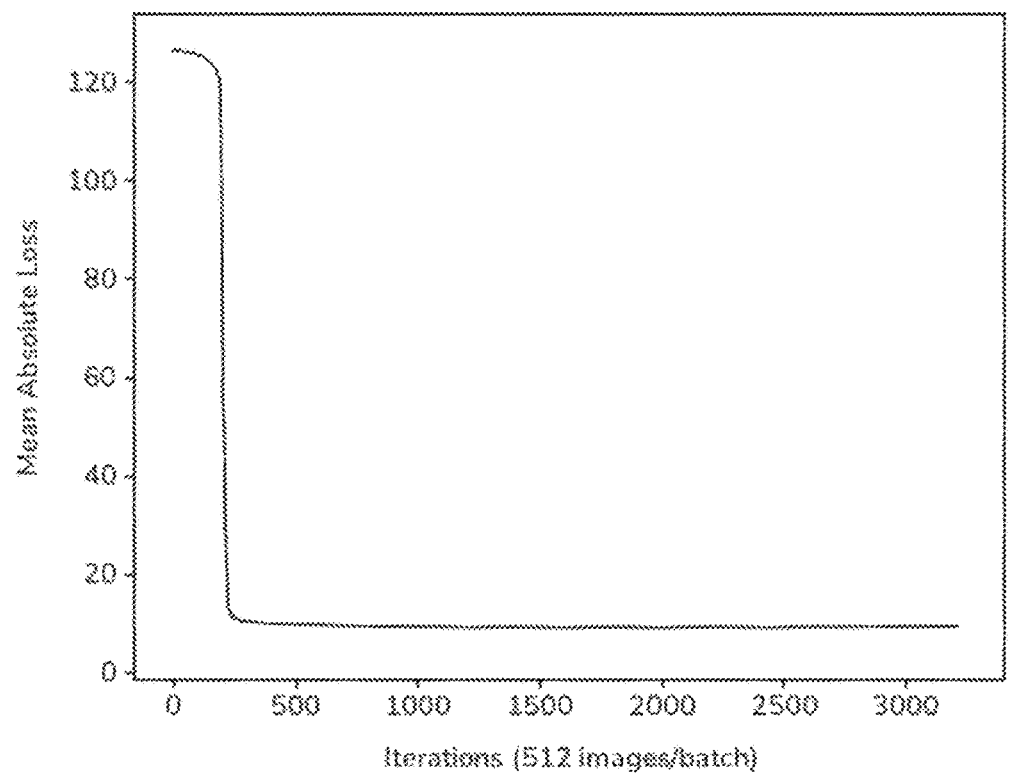

FIG. 7C

IMAGE-BASED SYSTEM AND METHOD FOR PREDICTING PHYSIOLOGICAL PARAMETERS

CROSS REFERENCE

The present application claims priority to U.S. Provisional Application No. 62/481,691, filed Apr. 5, 2017, which is incorporated herein by reference in its entirety.

TECHNICAL FIELD

The embodiments provided herein disclose an image-based method to predict physiological parameters, and more particularly, a method utilizing facial image of human being for the prediction of multiple physiological parameters, e.g., Body Mass Index (BMI), Basal Metabolic Rate (BMR), etc., of a person.

BACKGROUND

A facial image of a person carries information about the person to indicate his/her health status. Such information can be extracted to derive physiological parameters.

Body Mass Index (BMI) is used as a tool widely used across age and gender. People can be divided into four categories based on their values of BMI, namely, underweight, normal, overweight, and obese. Each of the categories links to certain health outlook of a person. With the rising attention of the public to health and longevity, the need to understand people's health condition through various biological measures of health risk becomes prominent. BMI, as one of biological indexes to reflect one's health condition, has been used in health examinations for many years. BMI draws wide interest in consumers and people looking for convenient, efficient, and accurate methods to understand their BMI as a critical health indicator. A similar trend has been observed for Basal Metabolic Rate (BMR), which provides an indication of the amount of energy per unit time that a person needs to keep the body functioning at rest.

On the other hand, the far-ranging use of personal mobile devices, such as smart phones, tablets, and portable digital assistants with cameras, enables people to easily and conveniently take photos of himself/herself or others at any time. Through observing an image of a person's upper body along with face, substantial information about that person's health condition can be observed.

A computational system may be used to extract such substantial information to help understanding health condition and physiological parameters of the person in the image. If a computational system can make a prediction with accuracy, efficiency and reliability of physiological parameters through facial images, users of the system are enabled to understand their health condition more conveniently and more reliably.

SUMMARY

Generally provided are a system and method for predicting physiological parameter of a human person based on one or more digital facial images. Preferably, a regression deep learning convolutional neural network (DNN) model is adopted. More preferably, a Network-in-Network (NiN) model is adopted as the neural network model for imaging processing. Three color channels of facial image are extracted to be used as three input parameters. The neural network has seventeen layers and generates estimated weight and height values of persons of facial images as outputs. The disclosed system and method can yield accurate, efficient, and reliable body mass index value predictions conveniently based on digital images provided by users.

In some embodiments, an image processing method of facial images is disclosed. A digital photo with at least a part of it as facial image of a person together with neck and upper shoulder image is viewed as a selfie image. The method starts from screening if an image received from a mobile device is qualified as a selfie image or not. Qualified images are further processed to a size of 224 by 224 pixels with three color channels. Processed images are frontal facial images with neck and upper shoulders of persons.

In some embodiments, a training method of a neural network model for prediction of physiological parameter of a person based on his/her facial image is disclosed. The method includes the step of obtaining of training data, which is a large quantity of facial images associated with corresponding accurate weight and height values of persons of the facial images. Such data may be available from public or commercial data base. The neural network model has seventeen layers for predicting original weight and height values of persons. By comparing the original predicted weight and height values to the associated accurate weight and height values of persons, the neural network model is configured to learn and modify parameters, layers, or coefficients to minimize the difference between original predicted weight and height values and the associated accurate weight and height values.

In some embodiments, a system for predicting body mass index value based on a facial image of a person is disclosed. The system comprises a server, an image processor, and a trained neural network model. The trained neural network model is configured to predict weight and height of the person based on the image received from the image processor, wherein the model is stored in the server and is accessible through Internet.

This summary is provided to efficiently present the general concept of the invention and should not be interpreted as limiting the scope of the claims.

BRIEF DESCRIPTION OF THE DRAWINGS

The above and other aspects of the present disclosure will become more apparent from the description of exemplary embodiments, taken in conjunction with the accompanying drawings.

FIGS. 2A and 2B are diagrams illustrating exemplary image pre-screening and pre-processing steps of image processor, consistent with embodiments of the present disclosure.

FIG. 7A is a tabulation illustrating exemplary layers of the trained regression NiN model, consistent with embodiments of the present disclosure.

FIG. 7B is a tabulation illustrating exemplary pre-set parameters of the regression NiN model for training purposes, consistent with embodiments of the present disclosure.

FIG. 7C is a diagram illustrating exemplary learning results of the regression NiN model, consistent with embodiments of the present disclosure.

DETAILED DESCRIPTION

Figure 1:
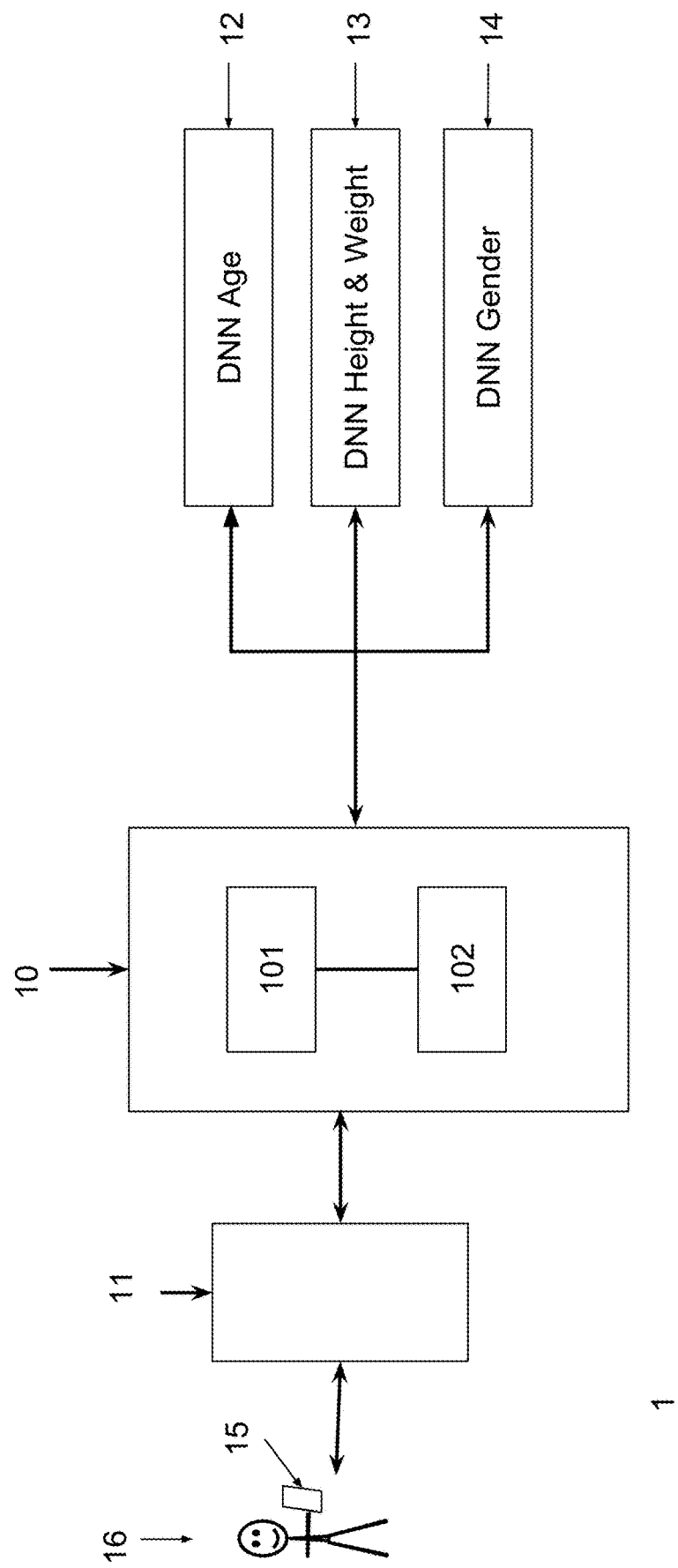
FIG. 1 is a diagram illustrating an exemplary physiological parameter prediction system based on a facial image, consistent with embodiments of the present disclosure.

Reference will now be made in detail to exemplary embodiments, examples of which are illustrated in the drawings. The following description refers to the accompanying drawings in which the same numbers in different drawings represent the same or similar elements unless otherwise represented. The implementations set forth in the following description of exemplary embodiments do not represent all implementations consistent with the invention. Instead, they are merely examples of apparatuses, systems, and methods consistent with aspects related to the subject matter as recited in the appended claims.

Reference is now made to FIG. 1, which is a diagram illustrating an exemplary physiological parameter prediction system based on a facial image, consistent with embodiments of the present disclosure. The system may be used to predict age, weight, height, and gender of a human, and the alike.

Physiological parameter prediction system 1 includes a physiological parameter determination block 10, a web server 11, a deep learning convolutional neural network (DNN) model to predict age 12, a DNN model to predict height and weight 13, and a DNN model to predict gender 14. As a web-based and cloud-based solution, web server 11 can be remotely located from an end-user 16 who sends in digital images and requests prediction through a device 15. End-user 16 can send in digital images from device 15 connected to web server 11. Device 15 can be an electronic device or a device capable of electronic connection, e.g., camera, smart phone, tablet, computer, smart watch, etc. Other appropriate devices will be understood by one of skill in the same art from the description herein. Device 15 can have its own photo taking function, can also store images received from other devices, and can access images in other devices. Such accessible images may be taken by another device. The image can be a digital image of a person with at least a part of it be facial image. The image could be full body image, upper body image, or facial image. Other suitable types of image for use in the physiological parameter prediction system 1 can be understood by one of skill in the art.

Figure 2A:
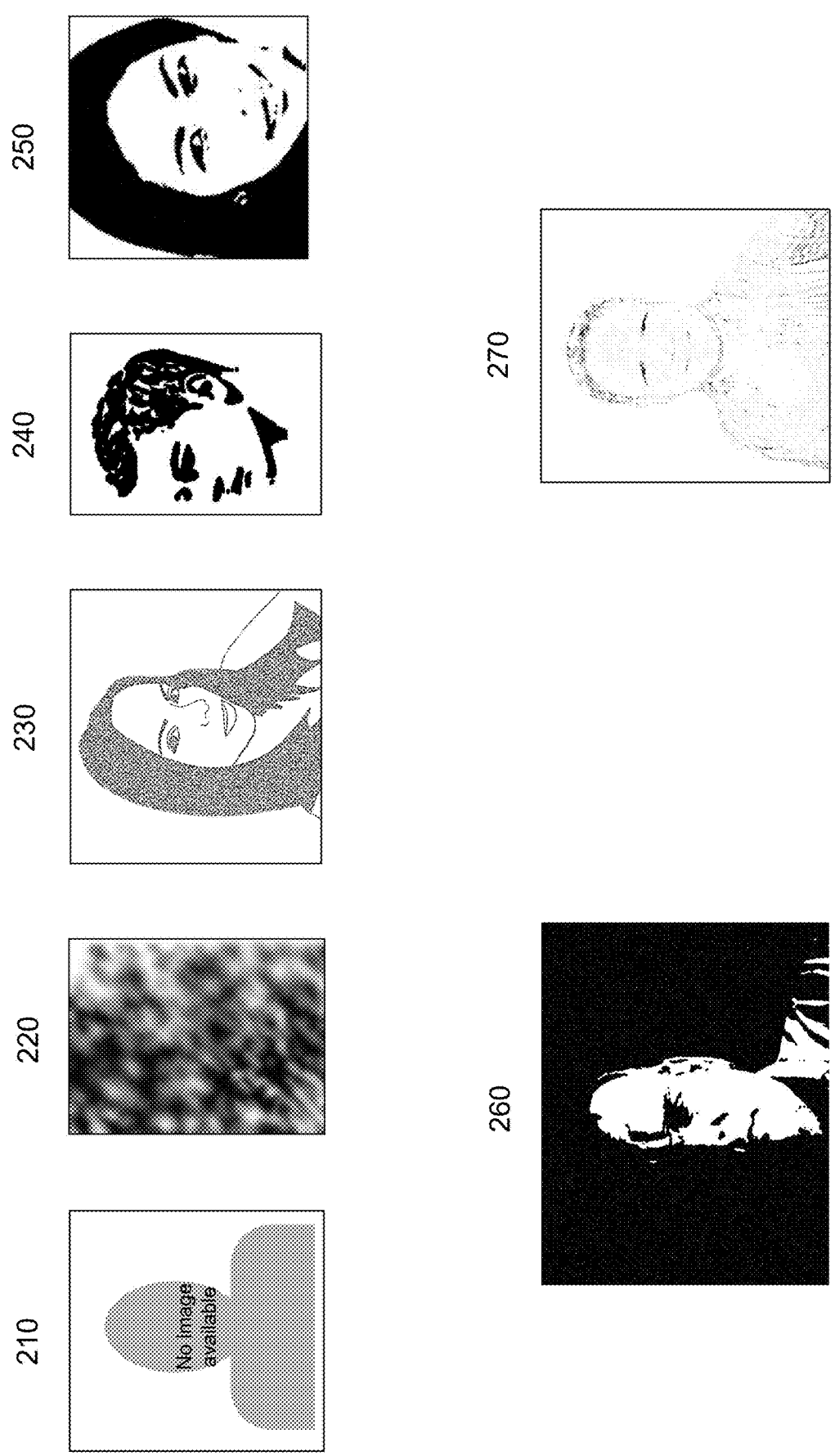

After receiving an image from device 15 and prediction request from end-user 16, web server 11 can send the received image and request to physiological parameter determination block 10. Physiological parameter determination block 10 comprises an image processor 101 and a predictor 102. The image processor 101 can be configured to pre-screen and pre-process received images. In application, a big portion of digital images are selfie photo images taken by end-users under leisure and pleasure conditions. Some of selfie images may have issues, thereby making these images unsuitable to be used to predict a physiological parameter (e.g., BMI, BMR, etc.) value accurately and reliably. Therefore, as shown in FIG. 2A, some images can be blank, e.g., blank image 210; some images can be black, e.g., black image 220; some images can be without a part or a full facial image, e.g., partial image 230; some images can be profile images taken from different angles, e.g., side profile image 240 and close frontal profile image 250; some images can have low contrast between foreground and background, e.g., low contrast image 260; while some images can provide too much shine on the contour of human face, e.g., shining image 270. Such images can be difficult to be used in physiological parameter prediction. There may be other conditions making an image unsuitable to be used in physiological parameter prediction without pre-process. Image processor 101 analyses image input and filters out images inappropriate to predict physiological parameter value accurately and reliably.

Images determined to be appropriate for BMI prediction in evaluation are processed in image processor 101 and adjusted to be suitable to predict a physiological parameter value (e.g., BMI value) in accordance with aspects of the disclosure for predicting BMI value. Predictor 102 can be configured to receive predicted age, weight, and height from DNN model of age 12, DNN model of height and weight 13, and DNN model of gender 14. Upon initiation, DNN model of age 12 predicts an age group classification of the person based on the received image of the person. Similarly, DNN model of weight and height 13 predicts the weight and height of a person based on the received image of the person, and DNN model of gender 14 predicts a gender group classification of the person based on the received image of the person. Values of predictions are returned to physiological parameter determination block 10 in response to the completion of predictions of these DNN models.

One exemplary physiological parameter value is a BMI value. Mathematically, BMI is defined as a human's weight in kilograms (kg) divided by his or her height in meters squared, or a linear conversion of weight, aka mass, and height units in pounds (lb) and inch (in) respectively, according to the below formula:

$$BMI = \frac{mass_{kg}}{height_m^2} = \frac{mass_{lb}}{height_{in}^2} \times 703$$

Predictor 102 is configured to determine a BMI value based on the formula and received weight and height values from DNN model of weight and height 13. DNN model of age 12 can be configured to predict the age group classification value based on received one or more images of the person prior to prediction of weight and height values. In some embodiments, DNN model of weight and height 13 can be configured to be based on the predicted age group classification value from DNN model of age 12. Physiological parameter determination block 10 returns calculated BMI value in response to web server 11. Physiological parameter determination block 10 may simultaneously send back age, weight, height, and gender prediction to web server 11. Web server 11 ultimately returns all values of prediction to device 17 of end-user 16.

The system architecture of FIG. 1 is meant to be exemplary and non-exclusive. One of skill in the art reasonably contemplate that other system configurations may be used in accordance with aspects of the present invention for predicting physiological parameter value of a person.

Reference is now made to FIG. 2A, which are diagrams illustrating exemplary image pre-screening and pre-processing steps of image processor 101, consistent with embodiments of the present disclosure. Image processor 101 is configured to identify and differentiate images with at least a part be a facial image of a person from those without at least a part be a facial image of a person. Image processor 101 can also be configured to identify and remove duplicates of identical images.

People take photos at various possible situations regardless of lighting condition, background, gestures, facial expressions, angles, etc. Based on physiological geometry of a person, arm or arms of the person taking the image may be captured in the photo. Arms may appear at the shoulder level, head level, or above head level. End-users may optionally use an extension apparatus, such as an extension stick. Similarly, the extension apparatus may appear at the shoulder level or head level of a person. Therefore, images can have various qualities for use with physiological parameter prediction.

The varying quality of facial images affects the effectiveness of prediction in accordance with aspects of the present disclosure. Blank image 210, black image 220, partial image 230, side profile image 240, close frontal profile image 250, low contrast image 260, and shining image 270 are not qualified to be used in such prediction. Image processor 101 is configured to identify and verify a person's face from a digital image, also known as facial recognition function.

Several face recognition algorithms can enable identifying facial features by image processor 101, such as geometric, photometric, 3-dimensional recognition, skin texture analysis, etc. In some embodiments of the disclosure, geometric facial feature recognition algorithm is adopted by image processor 101. Image processor 101 can be configured to first screen out selfie images that are not qualified for predicting BMI value in accordance with aspects of the present disclosure.

With reference to FIG. 2B now, image processor 101 can be further configured to process screened facial images qualified for prediction of physiological parameter. FIG. 2B illustrates a work flow of a method for pre-processing images. After pre-processing, digital images with a face are centralized and peripheral contents are cropped. Starting with a raw digital image, at step 201 a face of a person is recognized, at step 202 a facial contour is delineated, at step 203 a face mask is computed and cropped, and at step 204 the face is centralized. In some embodiments, raw image can be 1280*960 pixel resolution with 4:3 aspect ratio, but it is appreciated that any commonly accepted resolution and aspect ratio can be used.

In some embodiments of the disclosure, at step 201 a face of a person can be recognized by face recognition algorithm identifying geometric facial features and extracting landmarks from the image. A few facial landmarks can be identified, such as eyebrows, nose, mouth, and contour of a face.

Based on facial landmarks identified at step 201, a facial contour can be delineated at step 202. Facial contour points are centered along a middle line, connecting the outmost points of a face, with the lowest point be the top of the jaw, and the highest point be the top of eyebrow. At step 202, a center point of all identified facial landmark points can be determined. In some embodiments, the central middle point identified is overlapped with the physiological central point of a face of a person, the high point of nose of a person. A contour line of the upper head is drawn by mirroring the contour of the lower face. Subsequently, a minimum rectangle bounding all drawn points of a face can be drawn, e.g., rectangle 20A in FIG. 2B. Width and height of rectangle 20A can be determined.

Meanwhile, at step 202, a supplementary rectangle 20B is drawn based on weight and height of rectangle 20A. The width of supplementary rectangle 20B can be configured to indicate the width of shoulders of the person in the image. The four corner points of supplementary rectangle 20B can be derived by connecting the central middle point and predetermined facial contour points to the shoulder of the person. Hence, supplementary rectangle 20B can identify the left shoulder and right shoulder. Further, supplementary rectangle 20B can facilitate the drawing of a final rectangle 20C.

At step 203, final rectangle 20C is derived by extending minimum rectangle 20A and supplementary rectangle 20B. Final rectangle 20C can be used as a complete face mask, which is defined to represent the region of interest of a facial image for the prediction of physiological parameters.

At step 204 the face mask is cropped according to the region of interest identified by final rectangle 20C. The cropped face mask is zoomed and aligned to be a frontal facial image for the prediction of physiological parameters in accordance with embodiments of the disclosure. In some embodiments, the frontal facial image can be resized and converted to 224 by 224 pixels. Inputs to regression DNN model of weight and height 13 can be configured to be 224 by 224 pixels, with three color channels. In some other embodiments, input images can be resized from images of 256 by 256 pixels that have been cropped 16 pixels at left, right, top, and bottom sides. This cropping can be any 224 by 224 pixels window within a 256 by 256 image. In some embodiments, intensity value of images is scaled to −1.0 to 1.0, instead of 0 to 255. The scaling is done by the following formula.

$$\text{image} = ((\text{color}(x,y)/255.0)*2-0.5) \forall x,y \in \text{image}$$

After step 204, a facial image is pre-processed to be frontal facial image, which is ready for predictions of physiological parameters in accordance with embodiments of the present disclosure.

Figure 3:
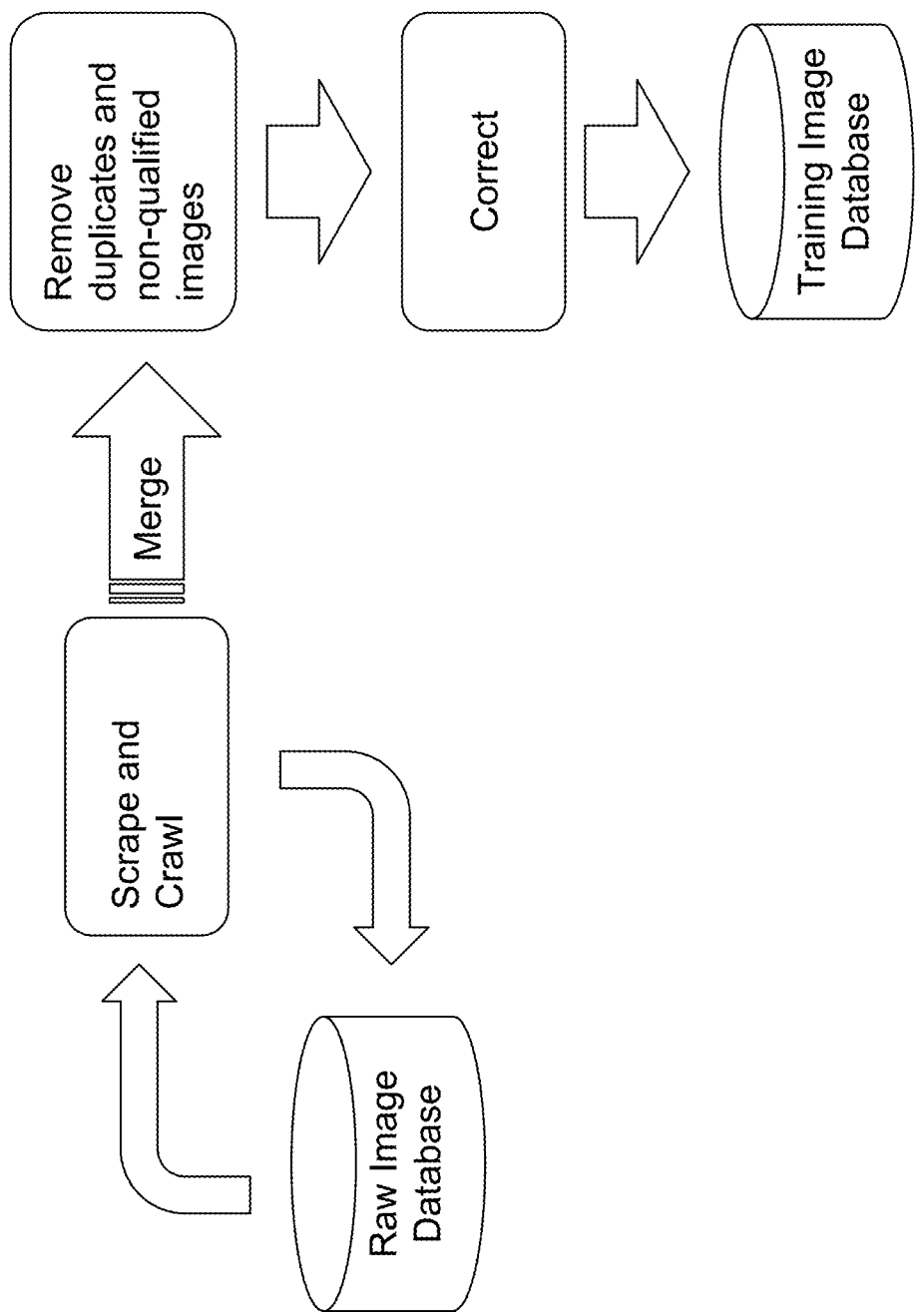
FIG. 3 is a block diagram illustrating a pipeline of data for obtaining a database suitable to be used as a training database for a facial image processing system, consistent with embodiments of the present disclosure.

Reference is now made to FIG. 3, which illustrates a pipeline of data for obtaining a database suitable to be used as a training database for a facial image processing system, consistent with embodiments of the present disclosure. In some embodiments, the image processing system for predicting BMI value of a person is configured to be a DNN-based machine learning system. DNN models used for predicting of age, height and weight, and gender, BMI values can be trained by large amounts of data to make accurate and reliable prediction. Images with corresponding weight and height values can be available in public database, which is treated as a raw image database and stored in a storage connecting to Internet. Images from a public dataset can be scraped and crawled back to the public dataset. Non-facial images can be removed at this stage. Moreover, duplicate images can be removed and/or merged. Thereafter, images are processed by correction process as described in detail in FIG. 2B. Therefore, a dataset of facial images for the training of a neural network model to predict values of physiological parameters of a person is obtained. In some embodiments, the dataset of facial images comprises corrected facial images and corresponding gender, age groups (for example, 10 years as a group), height, and weight information of the persons associated with the images.

Figure 4:
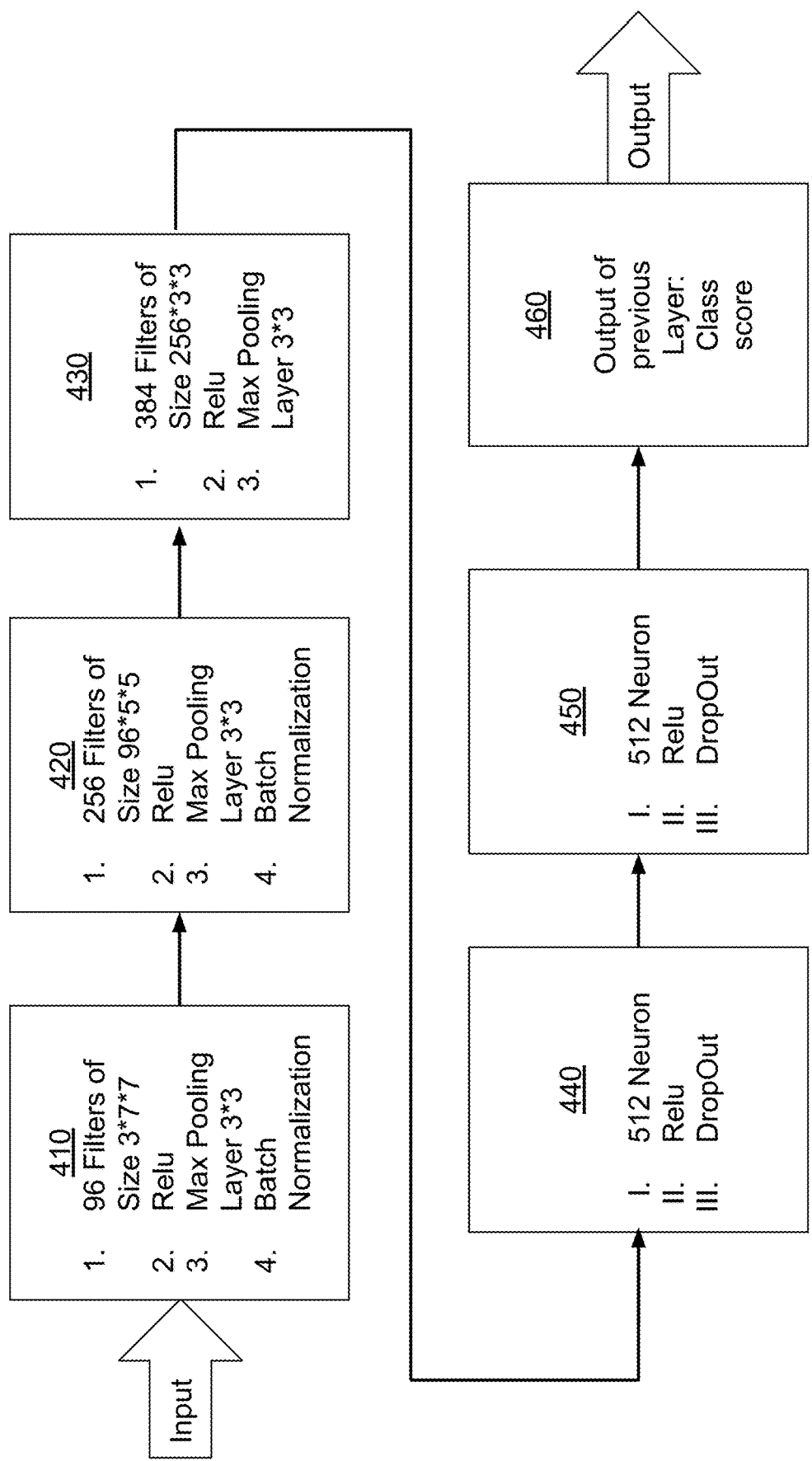
FIG. 4 is a schematic drawing illustrating an exemplary regression deep learning convolutional neural network model of age, consistent with embodiments of the present disclosure.

With reference to FIG. 4 now, an exemplary age group classification algorithm is demonstrated. Numbers of Layer of algorithm can be configured to vary. Age group classification is a factor for predicting physiological parameters like BMI value accurately and reliably in accordance with aspects of the current disclosure. A deep-learning based approach can be a very effective machine learning method to handle unconstrained imaging conditions most likely encountered in selfie images. In some embodiments, a deep convolutional neural network algorithm is adopted to handle unconstrained images.

Layer 410 can be configured to be a convolutional layer. In this layer, input image in three color (Red, Green, Blue) channels can be convoluted with 96 filters. Each of the 96 filters can be configured to be a matrix pattern in the size of 3*7*7. Thereafter, activation function, e.g., Rectified Liner Unit (ReLU), can be applied to every pixel of the image in three color channels. As a result of ReLU, an image pixel matrix is derived. The image pixel matrix can be further down sized in the step of Max Pooling by a pre-defined filter size. The filer usually can be configured to be a square, e.g., 3*3. Other downsizing layers may include Avg Pool, etc. The downsized data is then converted to a two-dimensional data and be normalized by Batch normalization. As a result of normalization, the matrix becomes a well-behaved matrix with mean value approximately equal to 0 and variance approximately equal to 1. As other convolutional layers, layer 420 and layer 430 can be configured to apply similar functions into the image pixel matrix.

In layer 440, the convoluted image pixel matrix is applied to a fully connected layer for liner transformation. The image pixel matrix is multiplied by a predetermined number of neurons, e.g., 512, so that the image pixel matrix is converted into a reduced dimensional representation with 512 values. In DropOut step, the reduced dimensional representation is defined by probability value. Layer 450 can be configured to apply similar functions into the reduced dimensional representation.

The last layer 460 can be another fully connected layer. In layer 460, the matrix of 512 values can be reduced to four final outputs, e.g., height, weight, age group classification, and gender. The outputs are the predictions of the neural network algorithm, which can be compared with values of the parameters associated with images for further training purpose of the algorithm.

In some embodiments, age estimation is based on calculation of ratios between measurements of parameters of various facial features. After facial features (e.g. eyes, nose, mouth, chin, etc.) are localized and their sizes and distances in between are measured, ratios between these facial feature measurement parameters are determined and used to classify the subject face into an age group class according to empirical rules defined by physiological researches.

In some embodiments, local features of a face can be used for representing face images and Gaussian Mixture Model is used to represent the distribution of facial patches. Robust descriptors can be used to replace pixel patches. In some embodiments, Gaussian Mixture Model can be replaced by Hidden-Markov Model and super-vectors are used for representing face patch distributions. In some embodiments, robust image descriptors can be used to replace local imaging intensity patches. Gabor image descriptor can be used along with a Fuzzy-LDA classifier, which may consider the possibility of one facial image belonging to more than one age group. In some embodiments, a combination of Biologically-Inspired Features and various manifold-learning methods are used for age estimation. In some embodiments, Gabor and local binary patterns (LBP) are used along with a hierarchical age classifier composed of Support Vector Machines (SVM) to classify the input image to an age-class followed by a support vector regression to estimate a precise age. Improved versions of relevant component analysis and locally preserving projections may be adopted. Those methods are used for distance learning and dimensionality reduction with Active Appearance Models as an image feature as well. In some embodiments, LBP descriptor variations and a dropout Support Vector Machines (SVM) classifier can be adopted.

Figure 5:
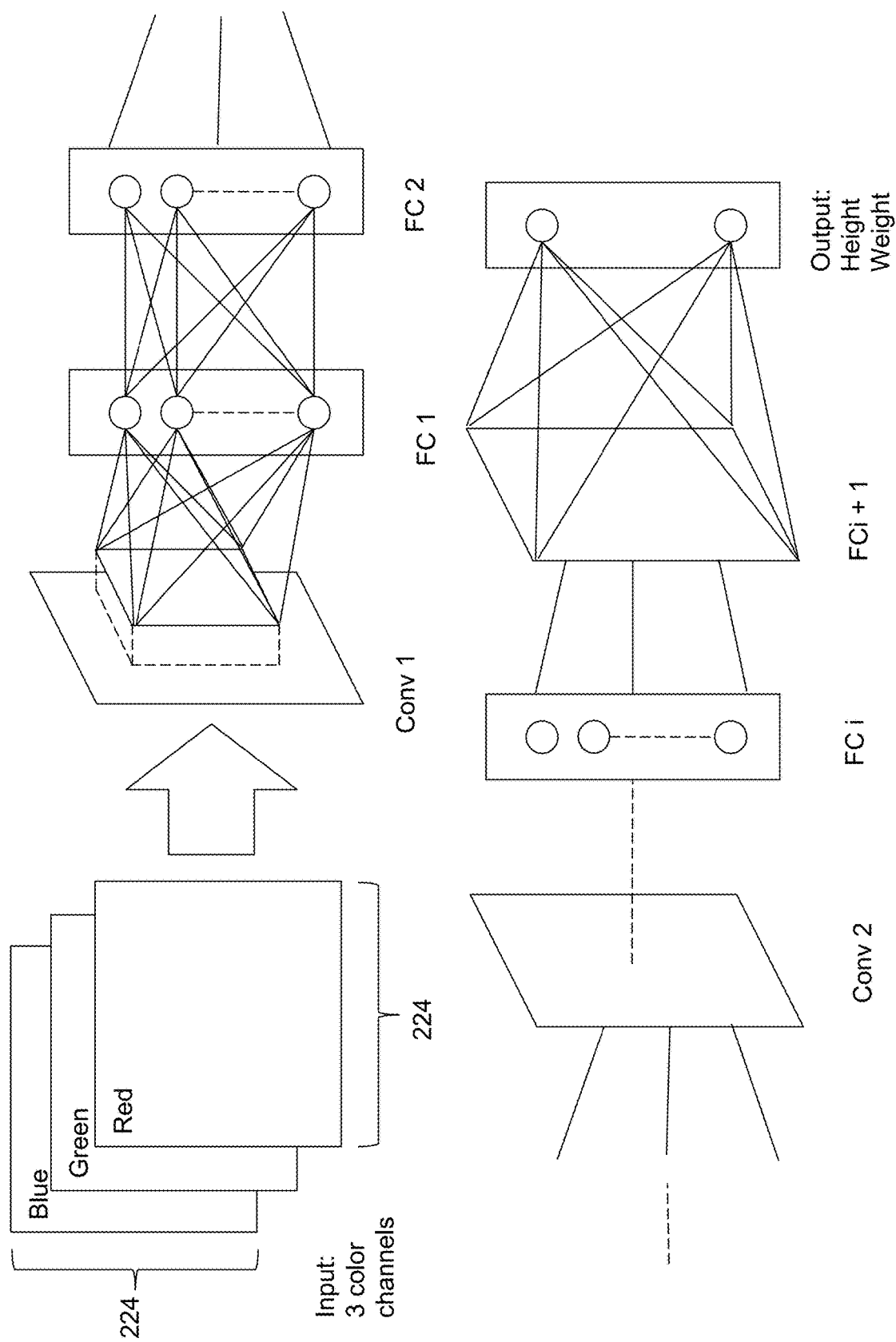
FIG. 5 is a schematic drawing illustrating an exemplary regression deep learning convolutional neural network model to predict height and weight, consistent with embodiments of the present disclosure.

Reference is now made to FIG. 5, which is a schematic drawing illustrating an exemplary regression DNN model to predict height and weight, consistent with embodiments of the present disclosure. In FIG. 5, $Conv_i$ is a convolution layer, and $FC_i$ is a fully connected layer.

In some embodiments, the model includes three parameters inputs, seventeen hidden layers, and two outputs of an image, height and weight of the subject person of the image. Pre-trained transfer learning models can be used. Images can be adjusted to have a resolution of 224*224. The first hidden layer can be a convolutional layer with size of 96*7*7. It can be configured to be followed by a ReLU Activation, a Max Pooling Layer with size of 3*3, a stride with size of 2*2, and a batch normalization. The second hidden layer can be a convolutional layer with size of 256*5*5. It can be configured to be followed by a ReLU Activation, a Max Pooling Layer with size of 3*3, and a batch normalization. The third hidden layer can be a convolutional layer with size of 384*3*3. It can be configured to be followed by a ReLU Activation and a Max Pooling Layer with size 3*3. Other hidden layers can be configured in a similar way and therefore are not repeated here.

Within the seventeen hidden layers, three hidden layers can be configured to be fully connected layers. FC6 (not shown in FIG. 5) can be configured to be the first fully connected layer with 512 neurons fully connected to the previous layer, followed by a ReLU Activation and a DropOut function. FC7 (not shown in FIG. 5) can be configured to be the second fully connected layer with 512 neurons fully connected to the previous layer, followed by a ReLU Activation and DropOut layer. FC8 (not shown in FIG. 5) can be configured to be the third fully connected layer with 16 neurons fully connected to the 1*512 output of FC7, yielding the un-normalized class values.

The regression DNN algorithm disclosed in FIG. 5 can be applied to build separate models on weight, height, age, and gender. Weight and height are required to calculate the predicted BMI or BMR values. Age and gender can be returned to digital devices and results are presented to end-users via digital devices.

Figure 6:
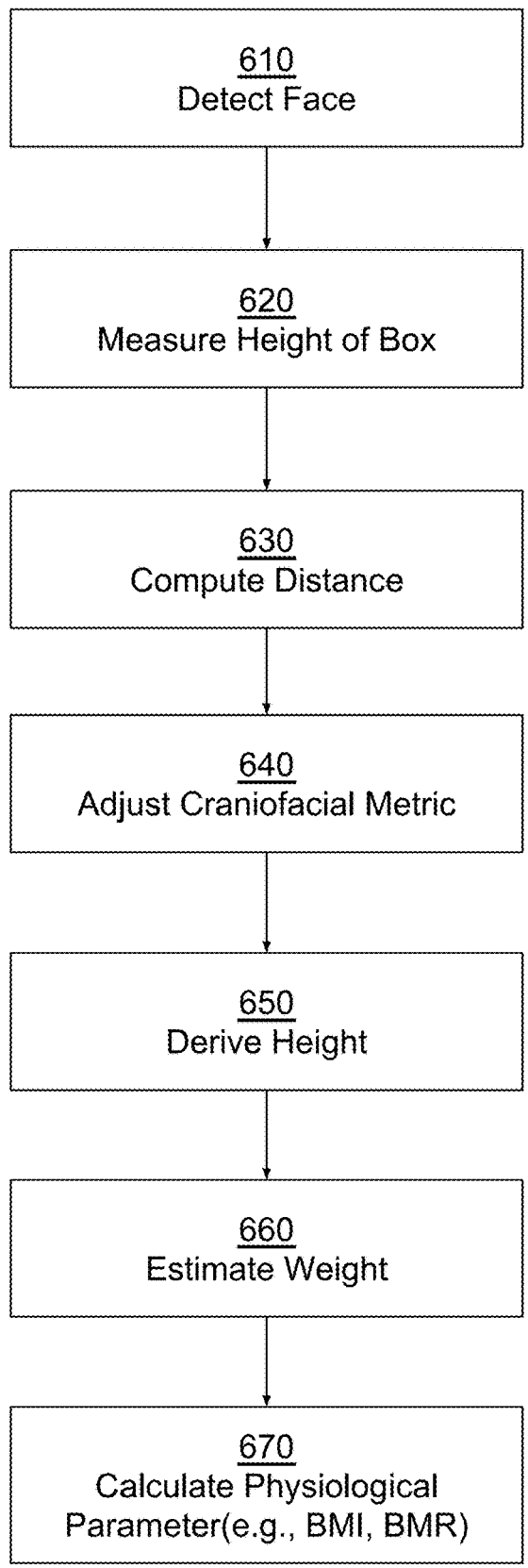
FIG. 6 is a schematic drawing illustrating an exemplary algorithm model to predict BMI value, consistent with embodiments of the present disclosure.

With reference to FIG. 6 now, a simplified algorithm is adopted to predict a physiological parameter value (e.g., BMI value) of a person, consistent with embodiments of the present disclosure. At step 610, a face can be detected from an adjusted image output by image processor 101. At step 620, height of the final rectangle box 22 can be measured. At step 630, the distance between the face associated with the image and the camera is computed, and local length and facial height is calibrated. Craniofacial Metric, a metric craniofacial variation, is adjusted at step 640 based on regression function for errors with known calibrated distance. At step 650, height of the person in the image is derived by multiplying the Craniofacial metric with the facial height. Thereafter, at step 660, weight of the person in the selfie image can be obtained by adjusting facial height by ideal body weight formula, e.g., J. D. Robinson formula. And physiological parameters, such as BMI and BMR values, can be calculated 670 from the derived weight and height values of the person.

FIGS. 7A, 7B, and 7C are relevant to the training to the DNN model described disclosed in detail description in FIGS. 4 and 5.

In some embodiments, the DNN is a supervised neural network. Input images are configured to be bound with label information or meta data representing the content of the images. In BMI prediction application, such meta data are weight and height of the person associated with the image. For each facial image used in the training process, height and weight values of the person in the image are associated. Therefore, the DNN receives feedback by comparing predicted weight and height values to associated weight and height values to further improve its prediction algorithm. To serve the supervised training purpose in accordance with aspects of the disclosure, images associated with weight and height values in the training database can be more than 100,000 images.

In some embodiments, FC6 layer can be chosen to be the layer closest to the output layer and express a set of features describing a facial image. These feature vectors in FC6 layer comprise more data in them than the original raw pixel values of the facial image. Many processes can be done on these feature vectors. In some embodiments, a NiN can be used as a Conventional Neural Network known to work well on image processing. Many other neural networks can be understood and chosen by a skill in the art without violating the principle stated in the embodiments of the disclosure.

Referring to FIG. 7A now, it depicts exemplary layers of the trained regression NiN model, consistent with embodiments of the present disclosure. The input and output dimensions are written as such to capture the number of parameters within the network. The Spatial Dimensions refer to the kernel width of the convolution, by the kernel height of the convolution, by the step of the convolution in the width dimension, by the step of the convolution in the height dimension.

In some embodiments, Stochastic Gradient Descent (SGD) is applied to train the NiN. This learning algorithm has two learning algorithms set by the user: Learning Rate and Momentum. These parameters are usually hand-tuned in the beginning iterations of SGD to ensure the network is stable. Training the regression NiN model can start from the parameters pre-set.

With reference to FIG. 7B, exemplary pre-set parameters of the regression NiN model for training purposes are shown, consistent with some embodiments of the present disclosure. The learning rates may not be adjusted over the duration of the batches. The mechanism of learning can be used to optimize the error between labeled weight and height values associated with a facial image and the outputs, estimated weight and height values of the subject person associated with the facial image, of the neural network. In mathematical optimization problem of BMI prediction based on facial images, this mechanism of learning is a loss function, which can also be cost function or objective function. A typical loss function for regression is Mean Absolute Error (MAE) given by equation as below.

$$MAE(x, y) = \frac{1}{n}\sum_{i=1}^{n}|x_i - y_i|$$

where x is the observed output of the neural network, and y is label information associated with the facial image (i.e., weight and height value of the subject person), and n is the number of images in the batch or dataset. MAE is not influenced by positive or negative errors, namely the direction of the error. This means the model can either over or under estimate weight and height. In some embodiments, this loss function model can also be Root Mean Squared or Mean Squared Error.

With reference to FIG. 7C, exemplary learning results of the model regression NiN model are shown, consistent with embodiments of the present disclosure. The Y-Axis is the value of the average MAE over the batch during the training phase. The X-Axis is the number of iterations, representing the number of pieces of images. It is observed that along with the increase number of images fed into the algorithm, which means the algorithm has been trained by more images, the error level has been decreased. After a certain number of images have been processed to train the algorithm, the error level reduces dramatically. After this cliff of training, the error level can be limited to a range of tolerance indicating that the trained algorithm is satisfactory for physiological parameters predictions.

Figure 8:
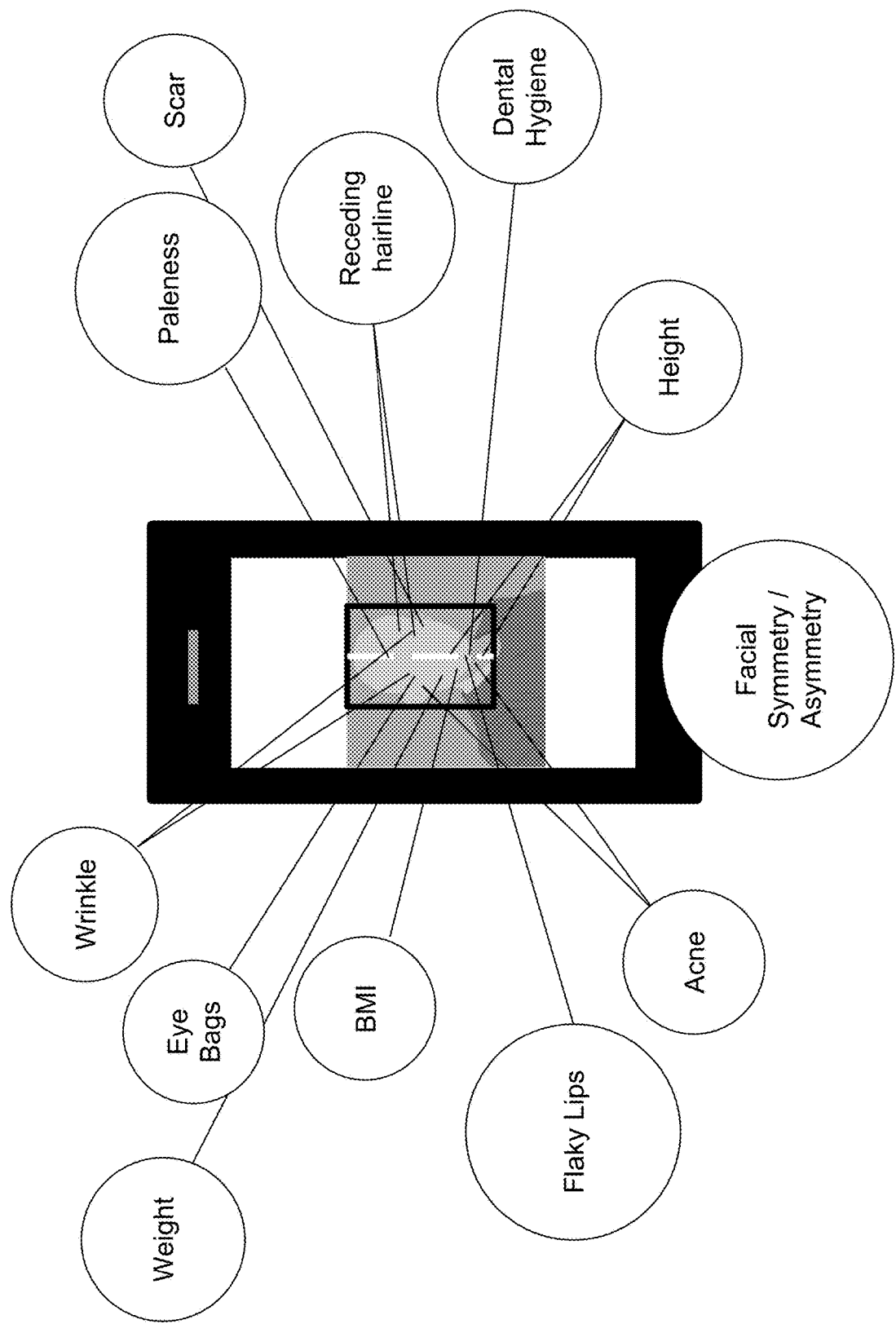
FIG. 8 is a diagram of a selfie image with a plurality of physiological parameters of a facial image of a person, consistent with embodiments of the present disclosure.

With reference to FIG. 8 now, in some embodiments, the regression DNN algorithm is utilized to predict other physiological parameters of a person in a digital image. For example, output of the algorithm is 0 to 100 scale of skin coloration, as paleness is relevant to and can be used to indicate anemia; or color tone of yellowness, as yellow tone is relevant to and can be used to indicate liver diseases; or color tone of bluishness, as a bluish tint in lips is relevant and can be used to indicate heart or lung diseases. For another example, output of the algorithm is 0 to 100 scale of flakiness of lips, as flakiness is relevant to and can be used to indicate dehydration. For another example, output of the algorithm is presence or absence of yellow spots on eyelids, as yellow spots on eyelids are relevant to and can be used to indicate cholesterol-filled lesions, called xanthelasmata, which links to a higher risk of heart disease. For another example, output of the algorithm is presence or absence of wrinkles in specific locations of a face, such as forehead, around eyes, and around mouth, or number of wrinkles in specific locations of a face, as wrinkles are relevant to and can be used to indicate aging. For another example, output of the algorithm is presence or absence of acnes on a face, or number of acnes on a face, as acnes are relevant to and can be used to indicate skin health conditions. For another example, output of the algorithm is 0 to 100 scale of symmetry/asymmetry of a face, as facial symmetry and asymmetry are relevant to and can be used as early indication of stroke. For another example, output of the algorithm is 0 to 100 scale of coloration of teeth; or color tone of yellowness of teeth, as coloration and yellow tone are relevant to and can be used to indicate dental health. For another example, output of the algorithm is 0 to 100 scale of scar, as scar is relevant to and can be one of the first sign of stroke or indicate injury. In another embodiment, output of the algorithm is presence or absence of eye bags and puffiness, as eye bags and puffiness are relevant to and can be used to indicate tiredness and chronic allergies. In another embodiment, output of the algorithm is 0 to 100 scale of receding hairline, as hairline is relevant to and can be used to indicate level of stress or infections on scalp.

In some embodiments, the regression DNN algorithm is utilized to predict some physiological parameters of a person in a video comprising a series of digital facial images. In some embodiments, outputs of video processing regression DNN algorithm can be heart rate variability, 0 to 100 scale of stress, or beats per minute of heart rate, which can be used to predict a person's heart or even mental health conditions. In some embodiments, outputs of video processing regression DNN algorithm can be eye movement, eye retinal movement, eyebrow movement, and a combination thereof, which can be used to predict myasthenia gravis, Bell's palsy, Horner's syndrome, crossed eye (more for babies), stroke, etc.

In some embodiments, the neural network algorithm can use eigenvectors in eigenfaces to extract features with Principal Component Analysis (PCA) by taking continuous video to study the longitudinal, infinitesimal changes in the face and correlate these subtle changes with diseases or health conditions. Such eigenvectors can be derived from a covariance matrix of a probability distribution over high-dimensional vector space of facial images. These eigenvectors can be processed by PCA analysis to convert a set of observations (e.g., infinitesimal and subtle changes of facial features) of possibly correlated variables into a set of values of linearly uncorrelated variables. The processed variables can be processed and reduced to one or more physiological parameters which may indicate diseases or health conditions.

It is appreciated that the disclosed embodiments may be implemented in software and/or a combination of software and hardware. For example, embodiments can be implemented by an application-specific integrated circuit (ASIC), a computer, or any other similar hardware device. In some embodiments, software program may be executed by one or more processors to implement the foregoing steps or functions. Software program (including a related data structure) may be stored in a computer readable medium, for example, a RAM, a magnetic drive, an optical drive, a floppy disk, or a similar device. In addition, some steps or functions of embodiments may be implemented by hardware, for example, a circuit that is coupled with a processor to execute the steps or functions.

In addition, a part of these embodiments may be applied as a computer program product, for example, a computer program instruction. When being executed by a computer, the computer program instruction may invoke or provide the methods and/or technical solutions disclosed through the operation of the computer. A program instruction that invokes the method of the present application may be stored in a fixed or removable recording medium, and/or is transmitted through broadcasting or by using a data stream in another signal-bearing medium, and/or is stored in a working memory of a computer device that runs according to the program instruction. In some embodiments, a disclosed apparatus includes a memory configured to store a computer program instruction and a processor configured to execute the program instruction. When the computer program instruction is executed by the processor, the apparatus is triggered to run the methods and/or technical solutions based on the foregoing multiple embodiments according to the present application.

The memory storing the instructions may be a computer readable medium in a form of a volatile memory, a random-access memory (RAM) and/or a non-volatile memory, for example, a read-only memory (ROM) or a flash memory (flash RAM). Memory is an example of computer readable medium.

The computer readable medium includes non-volatile and volatile media as well as movable and non-movable media, and may implement information storage by means of any method or technology. Information may be a computer readable instruction, a data structure, a module of a program or other data. An example of the computer storage medium includes, but is not limited to, a phase-change memory (PRAM), a static RAM (SRAM), a dynamic RAM (DRAM), another type of RAM, a ROM, an electrically erasable programmable ROM (EEPROM), a flash memory or another memory technology, a compact disc ROM (CD-ROM), a digital versatile disc (DVD) or another optical storage, a cassette tape, a magnetic tape, a disk storage or another magnetic storage device or any other non-transmission medium, and may be configured to store information accessible to a computing device. As defined herein, the computer readable medium does not include transitory media, for example, a modulated data signal or carrier.

Although the invention is illustrated and described herein with reference to specific embodiments, the invention is not intended to be limited to the details shown. Rather, various modifications can be made in the details within the scope of equivalents of the claims by anyone skill in the art without departing from the invention.

What is claimed:

1. A system for predicting physiological parameter of a person based on a facial image thereof, comprising:
    an image processor, electrically coupled with a network, configured to:
    receive from a digital device an image including facial and upper body features of a person;
    process the image to generate a frontal facial image;
    provide the frontal facial image, comprising the facial and upper body features, to a trained neural network model configured to predict weight and height of the person based on the facial and upper body features;
    receive predicted weight and height of the person from the neural network model;
    determine body mass index value associated with the person; and
    provide for display the determined body mass index value; and wherein
    the trained neural network model is a regression deep learning convolutional neural network model.

2. The system of claim 1, wherein the neural network model has three input parameters and seventeen hidden convolutional layers.

3. The system of claim 2, wherein the three input parameters are three color channels corresponding to one or more images.

4. The system of claim 1, wherein the regression deep learning convolutional neural network model is a Network-in-Network neural network model.

5. The system of claim 1, wherein said frontal facial image is provided via three color channels.

6. The system of claim 1, further comprising a server, electrically coupled with the network, wherein the trained neural network model is stored on the server.

7. The system of claim 1, further comprising a digital device configured to capture an image including a facial and upper body features of the person, wherein the digital device is electrically coupled with the network.

8. The system of claim 1, wherein the image processor is further configured to evaluate the image to determine if the image is a qualified image of the person.

9. A method for predicting physiological parameter of a person based on a facial image thereof, comprising:
    receiving a request for body mass index value;
    acquiring an image with at least facial and upper body features of a person; processing the image to a frontal facial image;

applying the frontal facial image, comprising the facial and upper body features, to a trained neural network model to predict weight and height of the person based on the facial and upper body features;

determining body mass index value based on the predicted weight and height; and providing, in response to the request, the determined body mass index value; and wherein said trained neural network model is a regression deep learning convolutional neural network model.

10. The method of claim 9, wherein the neural network model has three input parameters and seventeen hidden convolutional layers.

11. The method of claim 9, wherein the regression deep learning convolutional neural network model is a Network-in-Network neural network model.

12. The method of claim 9, wherein said frontal facial image is applied via three color channels.

13. A non-transitory computer readable medium including a set of instructions that are executable by one or more processors of a computer to cause the computer to perform a method for predicting body mass index value based on a facial image of a person, the method comprising:

receiving a request for body mass index value;

acquiring an image with at least facial and upper body features of a person; processing the image to a frontal facial image;

applying the frontal facial image, comprising the facial and upper body features, to a trained neural network model to predict weight and height of the person based on the facial and upper body features;

determining body mass index value based on the predicted weight and height; and providing, in response to the request, the determined body mass index value; and wherein said trained neural network model is a regression deep learning convolutional neural network model.

14. The method of claim 13, wherein the neural network model has three input parameters and seventeen hidden convolutional layers.

15. The method of claim 13, wherein the regression deep learning convolutional neural network model is a Network-in-Network neural network model.

16. The method of claim 13, wherein said frontal facial image is applied via three color channels.

17. A system for predicting physiological parameter of a person based on a facial image thereof, comprising:

an image processor, electrically coupled with a network, said image processor being configured for:

receiving from a digital device a captured image including upper body features of a person; said upper body features including a face and a neck and shoulders of said person, and said upper body features excluding body features that are lower than said shoulders of said person;

pre-processing said captured image to generate a pre-processed image, said pre-processed image being a frontal facial image, said frontal facial image including said upper body features, and said frontal facial image further excluding body features that are lower than said shoulders of said person;

providing said pre-processed image as input into to a trained neural network model, said trained neural network model being configured to predict weight and height of the person based on said pre-processed image; and receiving a predicted weight and height of the person from the neural network model.

18. The system of claim 17, wherein said pre-processed image is input into said trained neural network model via three color channels.

19. The system of claim 17, wherein a supplementary rectangle is employed to indicate a width of said shoulders of said person.

20. The system of claim 17, further configured for determining a predicted body mass index value associated with said person.

21. The system of claim 17, wherein said the trained neural network model is a regression deep learning convolutional neural network model.

22. The system of claim 21, wherein the regression deep learning convolutional neural network model is a Network-in-Network neural network model.

23. The system of claim 17, wherein said trained neural network model is trained by images of persons, each of said images including said upper body features of a person and excluding body features that are lower than said shoulders of said person, and each of said images being associated with a corresponding known weight value and a known height value values of each said person shown within each of said images of persons.

24. The system of claim 17, further comprising a server, electrically coupled with the network, wherein the trained neural network model is stored on the server.

25. The system of claim 17, further comprising a digital device configured to capture an image including a facial and upper body features of said person, wherein the digital device is electrically coupled with the network.

26. The system of claim 17, wherein the image processor is further configured to evaluate the image to determine if the image is a qualified image of said person.

* * * * *

UNITED STATES PATENT AND TRADEMARK OFFICE
CERTIFICATE OF CORRECTION

PATENT NO. : 11,026,634 B2
APPLICATION NO. : 15/946629
DATED : June 8, 2021
INVENTOR(S) : Walter De Brouwer et al.

It is certified that error appears in the above-identified patent and that said Letters Patent is hereby corrected as shown below:

In the Claims

In Claim 23, Column 14, Line 39, delete the word "values".

Signed and Sealed this
Eighteenth Day of October, 2022

*Katherine Kelly Vidal*

Katherine Kelly Vidal
*Director of the United States Patent and Trademark Office*